United States Patent
Arizmendi

[19]

[11] Patent Number: 6,112,936

[45] Date of Patent: Sep. 5, 2000

[54] MEDICAL GLOVE DISPENSING ENCLOSURE

[76] Inventor: Edward Louis Arizmendi, 12238 Madrona, San Antonio, Tex. 78245

[21] Appl. No.: 09/014,459

[22] Filed: Jan. 28, 1998

[51] Int. Cl.[7] .................................................. A47K 10/24

[52] U.S. Cl. .............................. 221/45; 221/63; 150/154; 206/389

[58] Field of Search ................................. 221/44, 34, 45, 221/46, 63, 33; 150/154; 206/409, 457, 389, 820, 438, 390, 205

[56] References Cited

U.S. PATENT DOCUMENTS

| | | | |
|---|---|---|---|
| 2,340,090 | 1/1944 | Vineburgh | 150/154 X |
| 4,002,264 | 1/1977 | Marchesani | 206/409 X |
| 4,387,832 | 6/1983 | Margulies | 221/63 |
| 4,570,820 | 2/1986 | Murphy | 221/34 |
| 4,773,532 | 9/1988 | Stephenson | 206/278 |
| 4,844,293 | 7/1989 | McLaughlin | 221/34 |
| 4,915,226 | 4/1990 | Keenan | 206/438 |
| 4,957,246 | 9/1990 | Kantor | 206/390 X |
| 5,165,567 | 11/1992 | Richardson et al. | 150/154 X |
| 5,285,927 | 2/1994 | Pruitt | 221/22 |
| 5,305,907 | 4/1994 | Richardson et al. | 150/154 X |
| 5,325,986 | 7/1994 | Richardson et al. | 150/154 X |
| 5,375,928 | 12/1994 | Yarng et al. | 150/154 X |
| 5,553,733 | 9/1996 | Rosenthal | 150/154 X |
| 5,562,229 | 10/1996 | Callahan | 150/154 X |
| 5,816,440 | 10/1998 | Shields et al. | 221/45 |

*Primary Examiner*—Christopher P. Ellis
*Assistant Examiner*—Patrick Mackey
*Attorney, Agent, or Firm*—Cox & Smith Incorporated

[57] ABSTRACT

An envelope made of tubular net material is stretched around a glove dispensing box or the like and closed on each end. Positioned immediately adjacent an opening in the dispensing box is a sphincter closure in the net material. The sphincter closure is created by cutting a hole in the net material and weaving an elastic band in a circle around the hole. Closure of the netting on either end of the dispensing box is accomplished by stitching, safety pins, or other such closures. It is preferable that one end of the envelope be permanently closed with stitching or a tied cord or the like. It is also preferable that the second end be releasably closed with any of a number of well-known bag or netting closure devices.

6 Claims, 3 Drawing Sheets

MEDICAL GLOVE DISPENSING ENCLOSURE

BACKGROUND OF THE INVENTION

1. Field of the Invention

The present invention relates generally to dispensing containers. The present invention relates more specifically to an enclosure for surrounding a dispensing container of the type which holds disposable medical gloves and the like. The present invention relates to an enclosing envelope that improves the reliability of single item dispensing from the enclosure.

2. Description of the Related Art

Latex medical gloves are typically dispensed from cardboard boxes much in the nature of tissue containers. Typically, there are three or four different sized gloves that are packaged separately in such boxes (small, medium, large, extra large). It is common to position three or four different boxes within a holder on a wall in hospital or clinic settings.

The openings on the dispensing boxes are typically large and frequently allow more than a single glove to be withdrawn at a time. It is not unusual for as many as four or five gloves to fall from the box when a single glove is pulled out. It would be desirable to create a dispensing aperture that controls the number of gloves released from the package. The present invention seeks to accomplish this and to reduce the waste associated with having to throw away gloves that fall to the floor.

U.S. Pat. No. 5,285,927 issued to Pruitt on Feb. 15, 1994, entitled "Container/Dispenser for Used Plastic Sacks." The Pruitt patent discloses a container/dispenser for plastic shopping bags that has an open top and an open bottom to which is secured a flexible lower section with a small opening through which the bags may be withdrawn one at a time.

U.S. Pat. No. 4,844,293 issued to McLaughlin on Jul. 4, 1989, entitled "Disposable Glove Dispensing Apparatus." The McLaughlin patent describes a container for disposable, thin plastic gloves that requires the gloves to be packaged in a planar unfolded condition. Access to the gloves is provided one at a time through an aperture in the container wall.

U.S. Pat. No. 4,773,532 issued to Stephenson on Sep. 27, 1988, entitled "Dispensing System for Sterile Gloves." The Stephenson patent describes an enclosure for dispensing flattened, sterile, surgical gloves that are positioned one after another in a long continuous roll. The roll is fed from the dispenser in a manner such as a paper towel dispenser would operate.

U.S. Pat. No. 4,915,226 issued to Keenan on Apr. 10, 1990, entitled "Hygienic Donning Packaging System for Surgical Gloves." The Keenan patent describes a donning system for individual medical surgical gloves that permits ease of insertion of the hand into the glove and the unrolling of the glove over the wrist and arm of the user.

U.S. Pat. No. 5,325,986 issued to Richardson et al. on Jul. 5, 1994, entitled "Bathroom Accessories." The Richardson et al. patent describes the combination of a rigid plastic container such as a facial tissue holder and a washable, pleated cloth bag having a shape conforming to the rigid plastic container. The cloth bag surrounds the rigid container and incorporates a retainer element near the opening of the rigid container. The opening serves the purpose of holding an item out from the container for ease of access by the user.

The problems associated with standard surgical glove dispensing devices such as those described above relate either to their complexity or to their inadequate dispensing of single items at a time. The various patents and products disclosed above in the prior art that achieve the dispensing of a single glove or single item at a time, do so at the expense of a complicated storage mechanism within the container. By either packaging the gloves in an orderly flattened form or positioning the gloves in single increments on a roll, the attempts in the past to solve the problem of single glove dispensing have done so only at high manufacturing and production costs.

Efforts in other fields unassociated with the surgical glove industry have focused on containers for tissue products and the like. In most instances the concern in the tissue product field is the maintenance of an item at the opening of the container ready for the user to access. The problem addressed in the tissue product field is that of preventing the user from having to reach into the container to extract an item. Thus, in cases where an enveloping enclosure surrounds the container, the objective of an elastic opening is to secure a single item in position for use.

The problems associated with the medical glove product dispensing field are not so much associated with positioning an item to be dispensed as the prevention of multiple items from being dispensed at a single time. The objective of the container envelopes described in the tissue dispensing field are not directed so much to the prevention of multiple items from being withdrawn from the container but the maintenance of a single item in a position to be withdrawn. The structure of the typical surgical glove container is such that access to the items inside is relatively easy through the large opening provided in the container. There is in fact no need to maintain an item in position near the opening as much as there is a need to prevent multiple items from being dispensed.

SUMMARY OF THE INVENTION

It is therefore an object of the present invention to provide an envelope for surrounding a medical glove dispensing container that prevents the dispensing of multiple gloves from the container at a single time.

It is a further object of the present invention to provide a reusable envelope for controlling the dispensing of medical gloves from a container that may be readily placed around and/or removed from a disposable glove dispensing container.

It is a further object of the present invention to provide an envelope for surrounding a disposable glove dispensing container that serves to catch multiple gloves that are inadvertently pulled from the container when a single glove is intentionally drawn from the container in such a manner as to prevent the multiple gloves from falling from the container and thereby being wasted.

It is a further object of the present invention to provide an envelope for surrounding a medical glove dispensing container that is inexpensive to manufacture and yet is reusable for a period of time without deterioration of its function.

The present invention involves the use of a tubular webbing that is stretched around a glove dispensing box and is closed on each end. Positioned immediately adjacent the opening of the dispensing box is a sphincter closure in the netting. The sphincter closure is created by cutting a hole in the netting and weaving an elastic band in a circle around the hole. Closure of the netting on either end of the dispensing box is accomplished by stitching, safety pins, or VELCRO type closures. It is preferable that one end of the tubular netting be permanently closed with stitching or a tied cord or the like. It is also preferable that the second end be releasably closed with any of a number of well-known bag or netting closure devices.

The concept involves opening the tubular netting and inserting the dispensing box. The netting stretches around the box and positions the sphincter opening immediately over the dispensing opening on the box. To withdraw a single glove, the user reaches through the sphincter opening into the box and pulls out a single glove. The netting around the opening prevents multiple gloves from falling out of the box onto the floor. Typically, the extra gloves are held within the netting much in the nature of a hammock surrounding the opening. In this manner, extra gloves are retained in a usable state even if they are withdrawn from the box. It is anticipated that the invention could involve a reusable netting that is placed around a new dispensing box as the old one is used up or could involve a disposable netting with a new one being utilized with each new dispensing box.

DESCRIPTION OF THE PREFERRED EMBODIMENT

Figure 1:
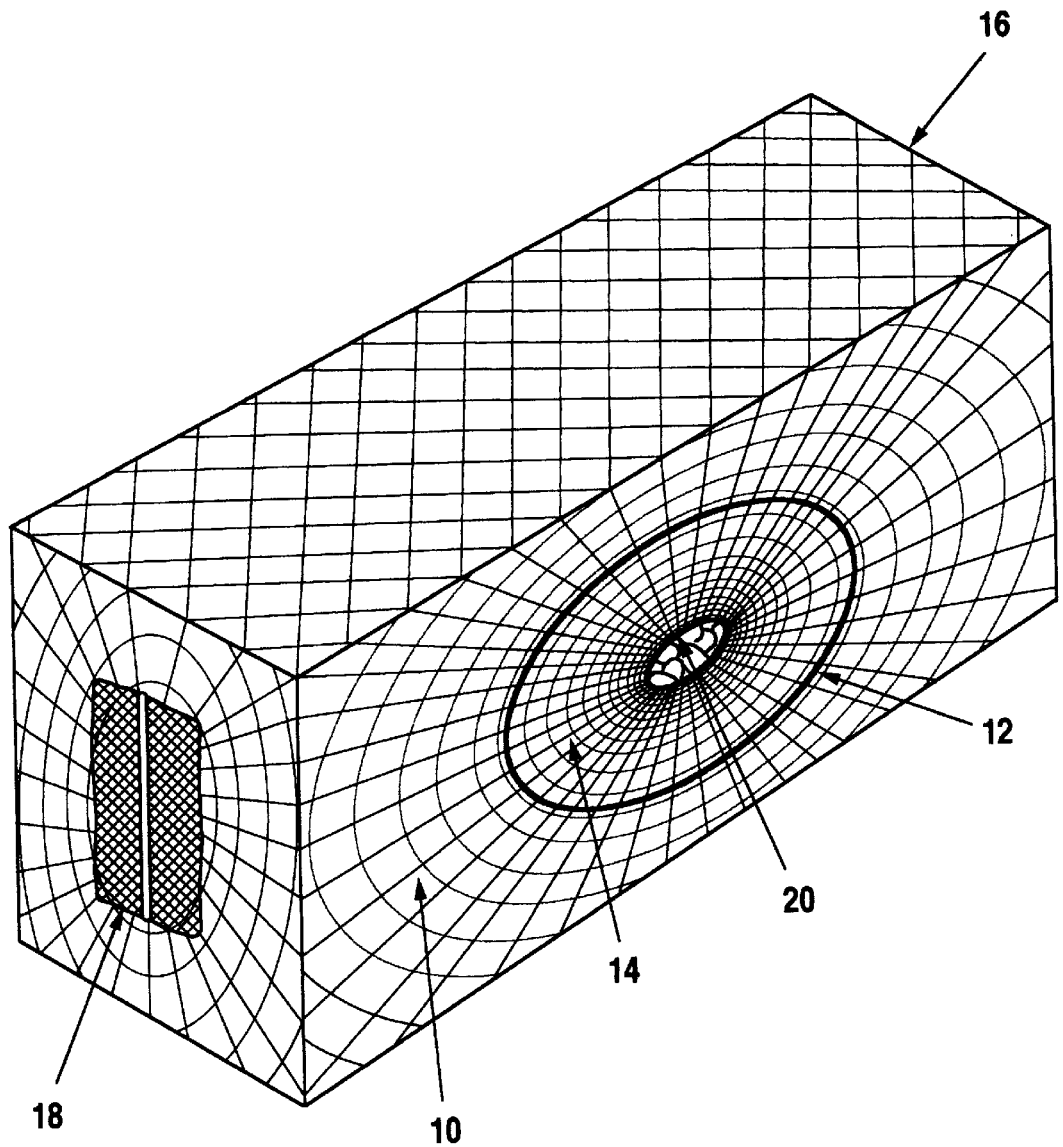
FIG. 1 is a perspective view of the envelope of the present invention shown in position about a medical glove dispensing container.

Reference is made first to FIG. 1 for a general description of the structure and function of the envelope of the present invention. The typical medical glove box (10) is rectangular, much in the nature of a cardboard tissue box, and generally includes an aperture (12) formed when a partial panel of one wall of box (10) is removed as along a perforated line. When aperture (12) is opened, access to medical gloves (14) within box (10) is provided.

When flexible mesh envelope (16) of the present invention surrounds box (10) and is secured with closure (18) in a manner described in more detail below, a smaller opening defined by elastic band (20) is positioned over aperture (12) in box (10). This smaller opening at elastic band (20) provides access to medical gloves (14) and yet reduces the size of the opening that might permit the inadvertent removal of multiple gloves (14).

Closure (18) is shown in FIG. 1 as a VELCRO™ type closure, although it may be any of a number of flexible closure mechanisms. In a simplest form, closure (18) might be a drawstring (as shown in FIG. 4) or a plastic tie wrap or the like.

Figure 2:
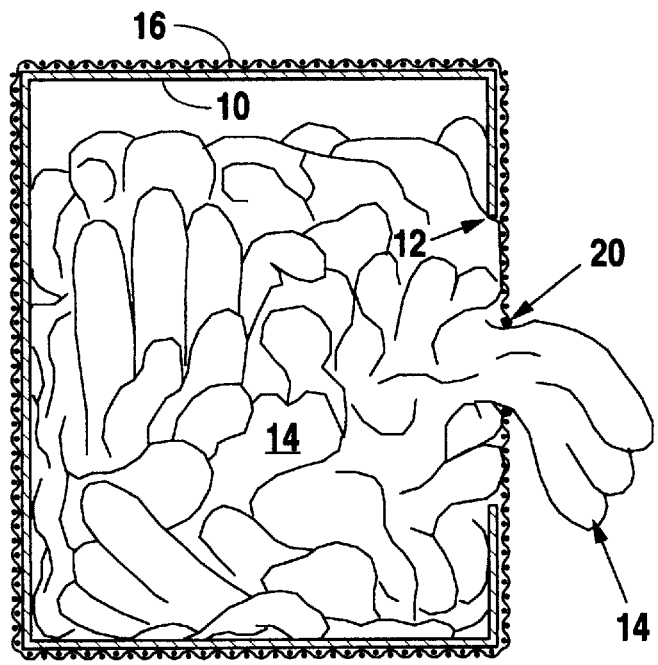
FIG. 2 is a cross-sectional view of the envelope of the present invention showing the method whereby items are retained in the opening of the invention ready to be dispensed.

Reference is made to FIG. 2 for a cross-sectional view of the present invention showing an array of medical gloves (14) contained within box (10) which is surrounded by flexible mesh envelope (16). At aperture (12) for box (10) elastic band (20) defines the narrower opening through which medical gloves (14) may be dispensed. Under normal conditions one or more medical gloves might be retained within elastic band (20) ready to be dispensed.

Figure 3:
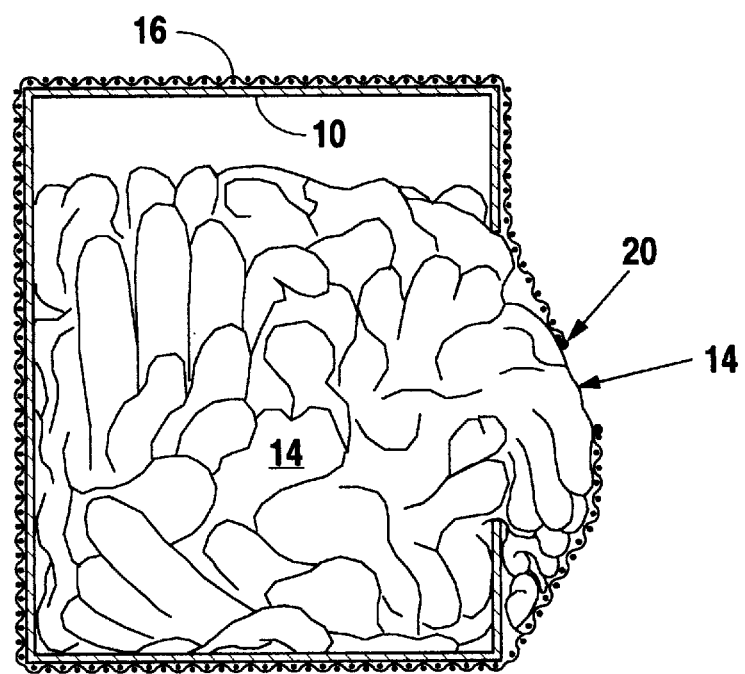
FIG. 3 is a cross-sectional view similar to that shown in FIG. 2 showing the method whereby the present invention retains multiple items in a usable position immediately outside the opening of the container.

FIG. 3 discloses a useful condition of the present invention whereby medical gloves (14), as they are withdrawn through the opening associated with elastic band (20), are accumulated between flexible mesh envelope (16) and box (10), outside of box (10) beyond aperture (12). The multiple number of medical gloves (14) thus held by envelope (16) would otherwise have fallen to the floor and would have been rendered unusable as a result of having been pulled through aperture (12) at the same time a single usable glove is accessed by the user. In this manner envelope (16) provides a secondary reservoir within which may be retained usable medical gloves (14) that are inadvertently withdrawn through aperture (12) from container (10).

Figure 4:
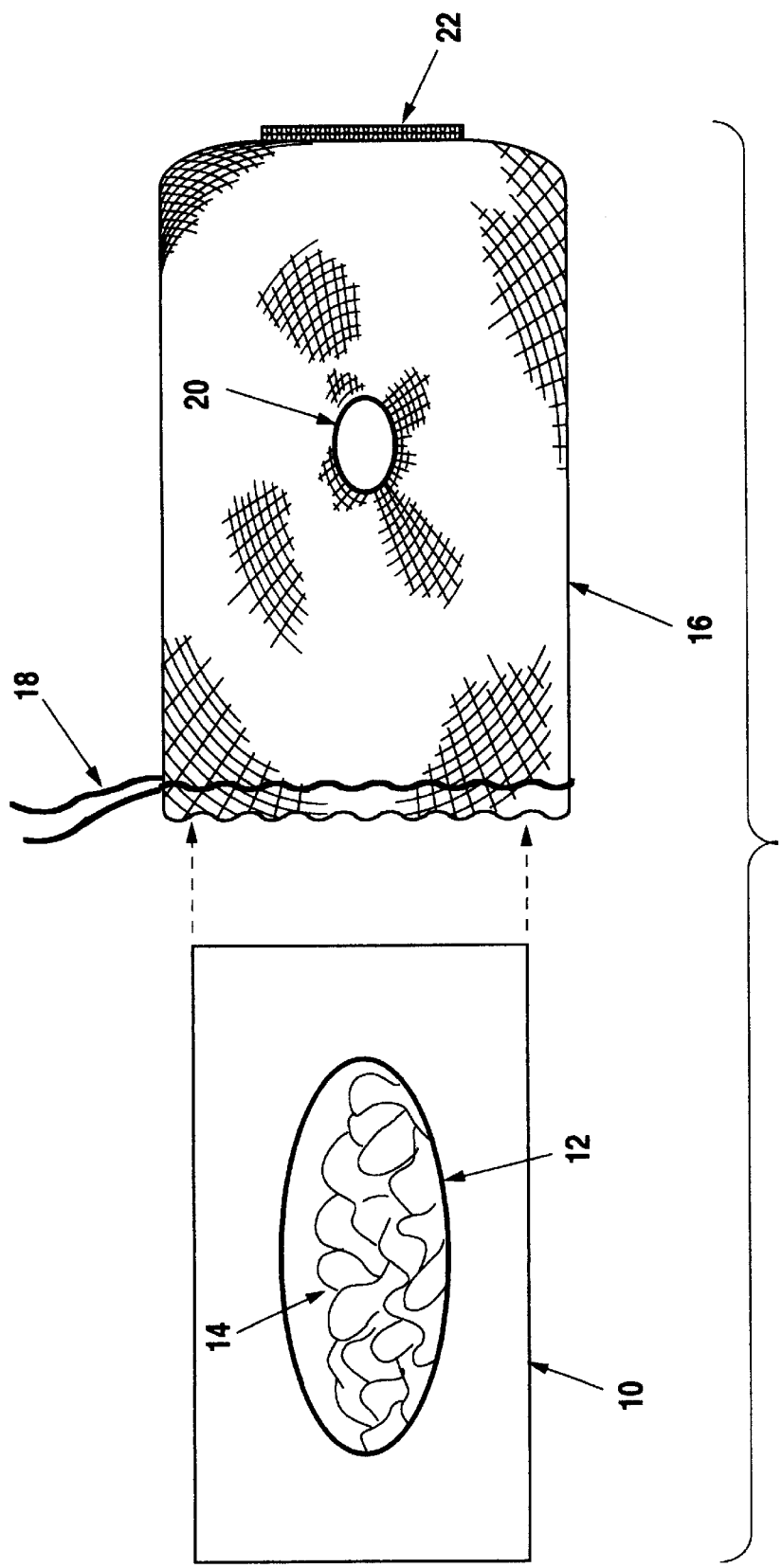
FIG. 4 is an exploded side view of the assembly shown in FIG. 1 wherein the method of placing the container within the envelope and securing it for use are described.

Reference is now made to FIG. 4 for a brief description of the method whereby envelope (16) of the present invention is designed to surround and envelope box (10) containing medical gloves (14). Closure (18) (shown here as a drawstring) is initially open in a manner that allows envelope (16) to expand to a size sufficient to permit the insertion of box (10) therein. Box (10) is oriented within envelope (16) such that elastic band (20) is positioned over the center of aperture (12) to provide access to medical gloves (14). Once box (10) is positioned within envelope (16) in this orientation and manner, releasable closure (18) is sealed tight such as with VELCRO™ surfaces (as shown in FIG. 1) or with a drawstring (as shown in FIG. 4) in order to secure envelope (16) in position around container (10). Permanent closure (22) (shown here as a VELCRO™ type closure), though it may be similar to releasable closure (18), is intended and may be designed not to be released since only one access is necessary to insert box (10) within envelope (16). Alternatively, closure (22) may be a permanently stitched seam closing envelope (16).

In alternative embodiments other means for inserting box (10) into envelope (16) are contemplated. With sufficient flexibility for elastic band (20) it is possible that envelope (16) would not have a releasable closure such as is shown with releasable closure (18). Instead, box (10) might be inserted through an expanded elastic band (20) and then oriented such that elastic band (20) is again positioned over aperture (12). While such a configuration is possible, given the objective of the present invention, it is likely that this method of inserting container (10) into envelope (16) would result in excessive strain and wear on elastic band (20) such that the lifetime use of the product would be diminished.

It is anticipated that a variety of materials might be used for envelope (16) in place of the mesh-like material described in the preferred embodiment. It is not necessary that the material be transparent to the user since the opening defined by elastic band (20) is usually sufficient to provide visual access to the product inside container (10). Any stretchable cloth-like material would be suitable for use as the material from which envelope (16) is comprised. The mesh-like material described in conjunction with the preferred embodiment is a readily available material commonly used in the medical field for the purpose of surrounding bandages and the like on the arms and legs of patients. The mesh-like product is manufactured and sold in tubular lengths of a cross-sectional diameter appropriate for use in the manner described with the present invention. Use of this product requires only the attachment of elastic band (20) in an appropriate position on the wall of the tubular material as well as the attachment of permanent closure (22) and releasable closure (18) at a first and second position along the length of the mesh tubing.

Alternative materials that meet the functional requirements described herein could be substituted for the tubular mesh material of the preferred embodiment. Likewise, it is anticipated that various other products beyond the medical glove field lend themselves to use in conjunction with the flexible opening envelope described herein. Any situation where items of a flexible nature such as gloves, bags, cloths, and the like with which it is desirable to dispense horizontally, as opposed to a gravity-fed vertical dispensing mechanism, could be utilized in conjunction with the present invention. It is to be understood that the objectives of the present invention are associated with the desire to dispense items easily in a readily accessible horizontal opening without the problem of dispensing multiple items and the resultant waste of products.

I claim:

1. An envelope for surrounding a container, said container having an aperture through which items within the container may be removed, said envelope comprising:

a length of cylindrically shaped mesh fabric sized so as to stretch over and envelop said container and generally conform to walls which define said container, said length of cylindrically shaped fabric having first and second open ends and a dispensing aperture at a point in said fabric cylinder between said first and second open ends;

an elastic band positioned around said dispensing aperture said elastic band defining said dispensing aperture to be sized and located in a position appropriate for orientation over and partial obstruction of said aperture of said container when said envelope is positioned around said container;

a releasable closure positioned on said first open end of said length of cylindrically shaped fabric for permitting the expansion of said first open end of said fabric cylinder sufficient for insertion of said container and thereafter for closing said first open end of said fabric cylinder so as to secure said container within said envelope; and a permanent closure positioned on said second open end of said length of cylindrically shaped fabric for closing said second open end of said fabric cylinder so as to secure said container within said envelope;

wherein said elastic band defines a flexible aperture through which items within said container might be removed and wherein multiple items inadvertently withdrawn through said aperture of said container are retained by said cylindrically shaped fabric partially obstructing said aperture of said container.

2. The envelope of claim 1 wherein said items to be dispensed from said container are latex gloves.

3. The envelope of claim 1 wherein said releasable closure comprises a releasable drawstring threaded about said first open end of said cylindrically shaped fabric.

4. The envelope of claim 1 wherein said releasable closure comprises matching lengths of hook and loop surfaces sewn about said first open end of said cylindrically shaped fabric.

5. The envelope of claim 1 wherein said permanent closure comprises a secured drawstring threaded about said second open end of said cylindrically shaped fabric and drawn tight prior to positioning said envelope over said container.

6. The envelope of claim 1 wherein said elastic band is sewn on to said fabric around said dispensing aperture.

* * * * *